(12) United States Patent
Chien et al.

(10) Patent No.: US 11,270,786 B2
(45) Date of Patent: Mar. 8, 2022

(54) CONTEXT-BASED PERSONALIZED ACTIVITY SCHEDULE

(71) Applicant: International Business Machines Corporation, Armonk, NY (US)

(72) Inventors: Yi-Chun Chien, Long Island City, NY (US); Colin Doms, Columbus, OH (US); Karina Elayne Kervin, Albany, NY (US); Elisa B. von Marschall, Charleston, SC (US)

(73) Assignee: International Business Machines Corporation, Armonk, NY (US)

( * ) Notice: Subject to any disclaimer, the term of this patent is extended or adjusted under 35 U.S.C. 154(b) by 400 days.

(21) Appl. No.: 16/452,816

(22) Filed: Jun. 26, 2019

(65) Prior Publication Data

US 2020/0411159 A1    Dec. 31, 2020

(51) Int. Cl.
| | |
|---|---|
| *G06F 3/048* | (2013.01) |
| *G16H 20/30* | (2018.01) |
| *G06F 3/01* | (2006.01) |
| *G01W 1/00* | (2006.01) |
| *G06F 1/16* | (2006.01) |

(52) U.S. Cl.
CPC ............. *G16H 20/30* (2018.01); *G01W 1/00* (2013.01); *G06F 1/163* (2013.01); *G06F 3/011* (2013.01); *G06F 3/017* (2013.01)

(58) Field of Classification Search
CPC ......... G16H 20/30; G01W 1/00; G06F 1/163; G06F 3/011; G06F 3/017
See application file for complete search history.

(56) References Cited

U.S. PATENT DOCUMENTS

| | | | |
|---|---|---|---|
| 7,212,922 B1 | 5/2007 | Longacre | |
| 7,383,130 B1 | 6/2008 | Koosam | |
| 8,938,218 B2 | 1/2015 | Pande | |
| 9,808,670 B2* | 11/2017 | Hoffman | G06F 1/1698 |
| 11,069,277 B2* | 7/2021 | Uemura | G01S 5/0027 |
| 11,148,007 B2* | 10/2021 | Williams | A63B 71/0622 |
| 11,152,098 B2* | 10/2021 | Sun | A63B 24/0075 |
| 11,152,100 B2* | 10/2021 | Crowley | G06F 1/1698 |
| 11,169,660 B2* | 11/2021 | Gupta | G06F 3/04817 |
| 11,209,957 B2* | 12/2021 | Dryer | G06F 3/04883 |
| 11,216,119 B2* | 1/2022 | De Vries | G06F 3/0485 |

(Continued)

FOREIGN PATENT DOCUMENTS

| | | | | |
|---|---|---|---|---|
| EP | 2363178 A2 * | 9/2011 | | G09B 19/0038 |
| WO | 2000068854 A1 | 11/2000 | | |

OTHER PUBLICATIONS

"Under Armour and IBM to Transform Personall Heallth and Fiitness Powered by IBM Watson," IBM News room, Las Vegas, NV—Jan. 6, 2016. 6 pages. <https://www-03.ibm.com/press/us/en/pressrelease/48764.ws>.

(Continued)

*Primary Examiner* — David Phantana-angkool
(74) *Attorney, Agent, or Firm* — Stephen R. Yoder

(57) ABSTRACT

A schedule for performing physical activities is generated by a physical activity model. The model draws from activity data, environmental data, and physical data collected during performance of identified physical activities. Weather forecasts for a particular region and time range drive the model to produce the performance schedule during the time range.

15 Claims, 7 Drawing Sheets

(56) References Cited

U.S. PATENT DOCUMENTS

| | | |
|---|---|---|
| 2015/0113417 A1 | 4/2015 | Yuen |
| 2015/0324751 A1 | 11/2015 | Orenstein |
| 2016/0117372 A1 | 4/2016 | Krafft |
| 2017/0072264 A1* | 3/2017 | Hoffman ............... G16H 20/30 |
| 2018/0249948 A1 | 9/2018 | Grabow |
| 2020/0411159 A1* | 12/2020 | Chien ..................... G06F 1/163 |
| 2021/0169417 A1* | 6/2021 | Burton .............. A61B 5/02055 |

OTHER PUBLICATIONS

"Location-based reports—Met Office". Oct. 23, 2015. 2 pages. <http://www.metoffice.gov.uk/construction/location-based-reports>.

"Meet Your New Running Partner—OutSider, a Weather-centric App for Runners and Outdoor Enthusiasts" Jun. 25, 2014 Press Release (/TAXONOMY/TERM/2). 4 pages.

"Online Machine Learning," Wikipedia, Sep. 6, 2016. 11 pages, <https://en.wikipedia.org/w/index.php?title=Online_machine_learning&oldid=738051875>.

"Outsider—running, jogging, walking, and cycling app for exercise and workout tracking on the App Store on iTunes". May 28, 2015, Internet Archive WaybackMachine, © The Weather Channel, 4 pages. <https://itunes.apple.com/us/app/outsider-running-jogging-walking/id889905206?mt=8>.

Blum, Avrim, "Online Algorithms in Machine Learning" Chapter 14 in "Online Algorithms: the state of the art", Fiat and Woeginger eds., LNCS #1442, 1998. 20 pages.

Carson, Chris, "Planning for adverse weather in Construction Projects" Published on Jun. 4, 2010. 36 pages. <https://www.slideshare.net/hilalitani/planning-for-adverse-weather-in-construction-projects>.

Laskov et al. "Lecture 8 Online and Incremental Learning" Advanced Topics in Machine Learning, 2012. Tübingen, German. 3 pages.

Theodoridis, Sergios, "Machine Learning: A Bayesian and Optimization Perspective" Chapter 5: Stochastic Gradient Descent—The LMS Algorithm and its Family. Elsevier Science and Technology Books, Inc., Elsevier Ltd. (c) 2015. 61 pages.

* cited by examiner

CONTEXT-BASED PERSONALIZED ACTIVITY SCHEDULE

BACKGROUND

The present invention relates generally to the field of physical activity technology, and more particularly, to the guided performance of physical activities.

The effects of weather on individuals performing physical activities are varied, with some activities being undesirable and other activities being changed considerably according to weather conditions. The performance level of individuals participating in certain physical activities can either be reduced or improved by prevailing weather conditions. Air temperature has a significant impact on the efficiency of performing certain activities. High air temperature can cause various heat-related illnesses such as heat cramps and heat stroke, while very low air temperatures may lead to illnesses such as hypothermia. Some training regimes may include methods of heat acclimatization. Heat acclimatization improves performance levels and reduces the potentially fatal risk of heat stroke. High air temperatures also result in thinner air, which creates less drag on participants of some physical activities where air resistance plays a major role. Cold temperatures may cause muscle tightness, which could lead to unnecessary muscle strain. Cold air temperatures can also lead to triggering asthmatic symptoms and/or dehydration for certain individuals. Some physical activities should be postponed due to localized precipitation. Some physical activities are too dangerous to be performed when the ground is damp or saturated with water because of the risk of injury from slipping. The effects of wind and poor visibility may also play a role in the performance level of certain physical activities.

Muscle strength, endurance, and coordination are important for physical activities. Several factors affect certain individuals participating in physical activities. Any injury is likely to have an adverse effect on the performance level of an individual. While the body heals from an injury, opportunities to move and build strength, stamina, and coordination are often missed. Diet, nutrition, rest, and hydration levels are also important factors that affect participating in physical activities at a physical or mental level.

SUMMARY

In one aspect of the present invention, a method, a computer program product, and a system includes: monitoring a physical activity performed by a user wearing an activity tracker during a period of time, receiving activity data from the activity tracker, the activity tracker tracking physical movement of the user during the period of time, determining environmental data in which the physical activity occurs for the period of time, receiving physical data describing physical conditions of the user while performing the physical activity, generating a physical activity model that correlates the activity data, the environmental data, and the physical data chronologically over the period of time, identifying a weather forecast for a geographic region in which the user will be located at a specified time range, determining, for the specified time range, a set of physical activities for the user to perform including the physical activity, and generating a schedule for user to perform the physical activity during the specified period of time, the schedule being determined by the physical activity model according to the weather forecast.

DETAILED DESCRIPTION

Figure 1:
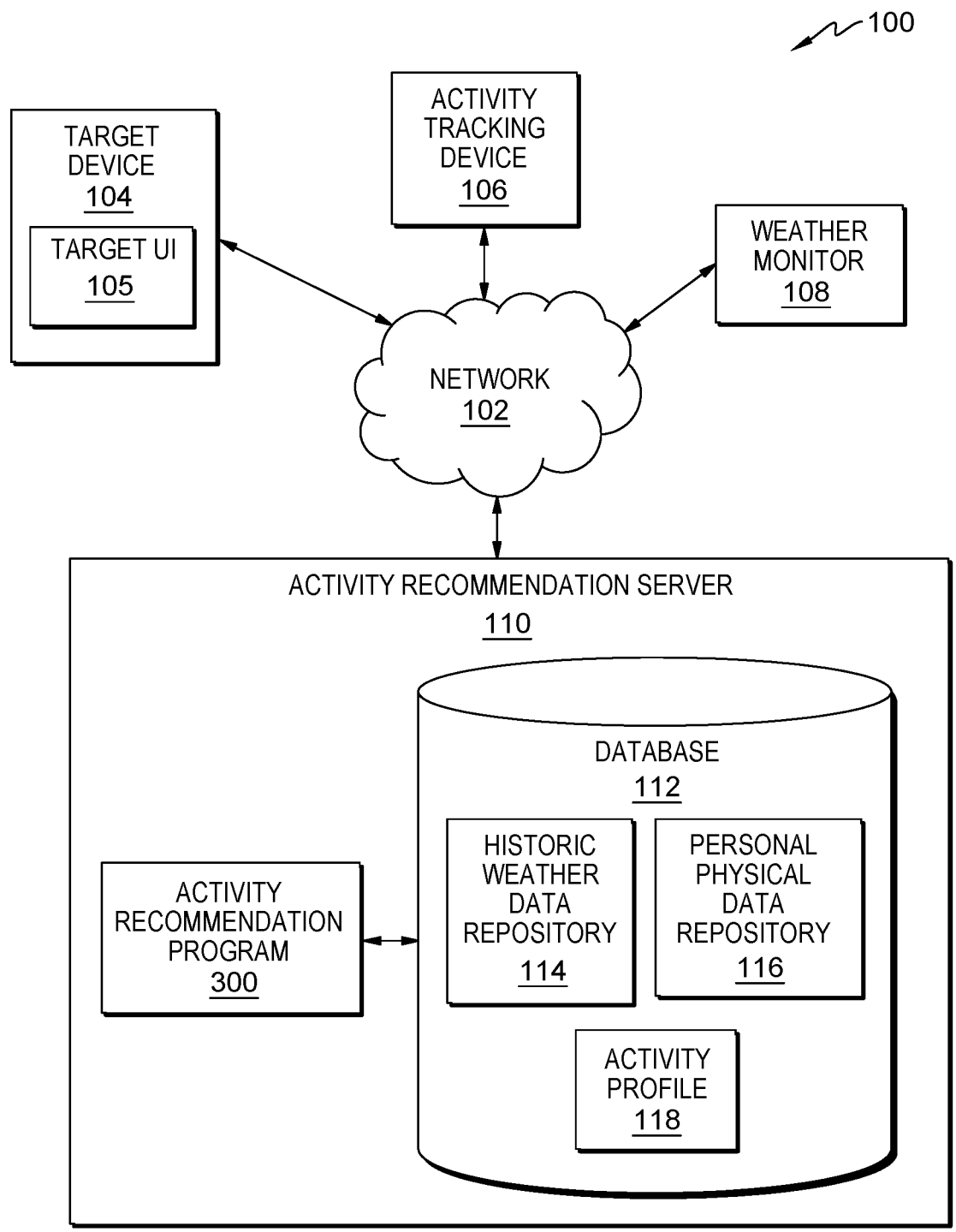
FIG. 1 is a functional block diagram view of a first embodiment of a system according to the present invention.

A schedule for performing physical activities is generated by a physical activity model. The model draws from activity data, environmental data, and physical data collected during performance of identified physical activities. Weather forecasts for a particular region and time range drive the model to produce the performance schedule during the time range.

Embodiments of the present invention recognize in some situations weather conditions impact performance levels of those engaging in outdoors activities. Weather factors affect people and teams differently. For example, some people are more prone to be affected by high air temperatures when running. In some cases, activities need to be planned in advance, such as when a team is to perform various tasks to complete a project. Advanced planning that assigns certain members of the team to some activities and other members of the team to other activities benefit from context-based activity schedules, as generated by some embodiments of the present invention. While research shows ideal conditions for a given activity for the general population, ideal conditions may differ in the context of a specific individual. Additionally, certain activities are discouraged in certain weather conditions. For example, running while a thunderstorm occurs would be unsafe for the runner.

Embodiments of the present invention provide a method to provide a customized physical activity schedule based on ideal weather conditions as illustrated by individual performance level data for certain physical activities. With the advent of wearable technology and the ability to log activity results, individualized analyses and performance schedules can be combined with historic weather data to align individual performance levels for certain physical activities with weather conditions. Physical activity data generated by personal fitness trackers can be beneficially correlated to weather conditions at the time of the physical activity to constantly improve physical activity schedules made in view of the current or forecasted weather conditions. These physical activity schedules can help people better plan exercise and activity events to improve fitness and productivity. The physical activity schedules may help a user identify what day, time, location, and type of physical activity is best to perform given the individual performance record of the user.

Some embodiments of the present invention provide advantages for recreation or business. Types of activities where context-based individual activity schedules may be applied include: running, biking, hiking, swimming, skiing, construction, and delivery services. For example, certain training regimes, such as triathlon training, require planning out exercise activities a week in advance. In an example pertaining to construction management, managers and employees may desire to keep construction on a carefully planned schedule to maximize productivity of the individual workers. In an example pertaining to individuals who want to increase health activities, patients following the advice of a physician may want to establish a plan to become more active. In an example pertaining to moving companies, moving coordinators may want to ensure safe and timely moves in relation to the weather.

Embodiments of the present invention will now be described in detail with reference to the Figures. It is to be understood that these embodiments are described only for the purpose of illustration and help those skilled in the art to understand and implement the present invention, without suggesting any limitation as to the scope of the invention. The invention described herein can be implemented in various manners other than the ones explicitly described herein.

FIG. 1 is a functional block diagram illustrating a computing environment for scheduling physical activities for a user based on physical activity data and weather data, in accordance with an embodiment of the present invention. For example, FIG. 1 is a functional block diagram illustrating computing environment 100. Computing environment 100 includes target device 104, activity tracking device 106, weather monitor 108, and activity recommendation server 110 connected over network 102. Target device 104 includes target user interface (target UI) 105. Activity recommendation server 110 includes activity recommendation program 300 and database 112. Database 112 includes historic weather data repository 114, personal physical data repository 116, and activity profile 118.

In various embodiments, activity recommendation server 110 is a computing device that can be a standalone device, a server, a laptop computer, a tablet computer, a netbook computer, a personal computer (PC), or a desktop computer. In another embodiment, activity recommendation server 110 represents a computing system utilizing clustered computers and components to act as a single pool of seamless resources. In general, activity recommendation server 110 can be any computing device or a combination of devices with access to some or all of target device 104, activity tracking device 106, and weather monitor 108, and with access to and/or capable of executing activity recommendation program 300. Activity recommendation server 110 may include internal and external hardware components, as depicted and described in further detail with respect to FIG. 6.

In this embodiment, activity recommendation program 300 is stored on activity recommendation server 110. In other embodiments, activity recommendation program 300 may reside on another computing device (e.g., target device 104), provided it can access and/or receive data from target device 104. In yet other embodiments, activity recommendation program 300 may be stored externally and accessed through a communication network, such as network 102. Operations executed by activity recommendation program 300 are discussed in greater detail with respect to FIG. 3.

In general, activity recommendation program 300 operates to identify physical activities for a user based on physical activity data and weather data. Activity recommendation program 300 uses an activity tracking device, such as activity tracking device 106, to identify physical activity data for the user of activity recommendation program 300. Conventional personal fitness trackers identify many user-specific physical activity data that may be beneficially used by the activity recommendation program. Additional physical activity data may be collected by other sensors incorporated into fitness trackers or as separate tracking devices. That is, multiple activity tracking devices may be deployed to collect and store physical activity data for use by the activity recommendation program. Activity recommendation program 300 identifies historic weather data corresponding to identified physical activity data. Historic weather data may be accessed by activity recommendation program 300 from a repository, such as historic weather data repository 114 on database 112. Activity recommendation program 300 identifies personal physical data associated with the user. The user may utilize a target device, such as target device 104, to input personal physical data. Personal physical data may be stored in a repository, such as personal physical data repository 116 on database 112.

Activity recommendation program 300 develops an activity profile for the user. The activity profile includes a physical activity model associating physical activity performance levels of a user with prevailing weather conditions when the physical activity is performed. The activity profile may be stored on a database, such as database 112. Activity recommendation program 300 identifies the weather forecast over a period of time. The weather forecast includes data collected from a weather monitor, such as weather monitor 108. Activity recommendation program 300 identifies personal activity objectives for the user. The user may utilize a target device, such as target device 104, to input personal activity objectives. Activity recommendation program 300 determines recommended activities for the user.

In general, activity recommendation program 300 determines recommended activities based on a combination of an activity profile of the user, weather forecast data, and personal activity objectives inputted by the user. Activity recommendation program 300 generates a schedule of activities for the user. The schedule may be organized by activity recommendation program 300 by how likely the user participates in the physical activity at optimal performance levels. In some embodiments, activity recommendation program 300 utilizes location information related to scheduled activities to display geographical routes for the user. In other embodiments, activity recommendation program 300 displays tips regarding scheduled activities.

Database 112 is a data repository that may be written to and read by activity recommendation program 300. Historic weather data, user personal physical data, and activity profiles may be stored to database 112. In some embodiments, database 112 may be written to and read by programs and entities outside of computing environment 100 in order to populate the repository with historic weather data, user personal physical data, and activity profiles. Contents of database 112, including contents of historic weather data repository 114, personal physical data repository 116, and activity profile 118, may be distributed among computing devices in FIG. 1.

Database 112 includes historic weather data repository 114, which can be accessed on database 112 by target device 104 to utilize historic weather data corresponding to physical activity data of a user. Historic weather data repository 114 may contain weather data associated with one or more external weather data sources. Weather data sources may be personal or commercial weather stations. A user of target device 104 may link weather stations relevant to the user's past locations. Historic weather data includes weather conditions such as air temperature, cloud coverage, humidity, precipitation, dew point, and pressure. A user of target device 104 may configure historic weather data repository 114 to contain historic weather data at certain intervals (i.e. constantly, every 15 minutes, hourly, etc.) In other embodiments, historic weather data repository 114 may be configured to be a web service that periodically, or as necessary, report historic weather data or software modules of activity recommendation program 300 that periodically query or interface with various services to obtain the historic weather data.

Database 112 includes personal physical data repository 116, which can be accessed on database 112 by target device 104 to utilize personal physical data of a user. Personal physical data repository 116 may contain personal physical data, sometimes referred to as demographic data, associated with a user. Personal physical data includes age, height, weight, and gender of a user. In some embodiments, a user of target device 104 may manually enter and/or update personal physical data to personal physical data repository 116. In other embodiments, personal physical data may be entered and/or updated into personal physical data repository 116 from a relevant third-party, such as a physician, a teacher, a parent or guardian, a family member or friend of the user, or an employer of the user.

Database 112 includes activity profile 118, which can be accessed on database 112 by a user of target device 104 to build an activity profile. The activity profile includes a physical activity model associating physical activity performance levels of a user with prevailing weather conditions when the physical activity is performed. The physical activity model may be used to recommend activities for a user. The physical activity model is based on a combination of a physical activity, monitored from activity tracking device 106, and historic weather data defining the prevailing weather conditions during the physical activity, collected from historic weather data repository 114. In some embodiments, activity-specific performance models in activity profile 118 may be updated by a relevant third-party, such as a physician, a teacher, a parent or guardian, a family member or friend of the user, or an employer of the user.

Some embodiments of the present invention develop the physical activity model as a table associating user-identified physical activity periods with weather conditions and physical activity data. Using the table, a user may define a desirable physical activity datapoint, or target data point and the activity recommendation program references current weather conditions or forecasted weather conditions of a target date and time to schedule a user-identified activity that has previously recorded the target data point. Alternatively, current weather is monitored by the activity recommendation program and whenever recorded weather conditions are associated with a target data point of the physical activity data, the program prompts the user to engage in the associated user-identified physical activity. Alternatively, physical activity types are pre-defined and determined according to detected physical movement of the user. Further, user-identified physical activity may be user-selected from a pre-defined list of physical activities.

It should be note that a physical activity model may be associated with a single user such that a team of users would have a set of physical activity models. The set of physical activity models may be accessed by an activity recommendation program operated by a central server that reports schedules to a team leader. Further, the table may include a performance level for the physical activity. The performance level may be derived from the set of physical activity data obtained during the period in which the physical activity is performed. Alternatively, the performance level is self-assessed at the end of the physical activity period is completed. As an example use case, a construction manager assigns team members physical activities that are both timely for the completion of a construction project and ideally suited for the individual according to previously recorded physical activity data and/or performance levels.

Network 102 can be, for example, a local area network (LAN), a wide area network (WAN) such as the Internet, or a combination of the two, and may include wired, wireless, fiber optic or any other connection known in the art. In general, network 102 can be any combination of connections and protocols that will support communications between activity recommendation server 110 and target device 104, in accordance with a desired embodiment of the present invention.

In various embodiments, target device 104 is a computing device that can be a standalone device, a server, a laptop computer, a tablet computer, a netbook computer, a personal computer (PC), a desktop computer, a personal digital assistant (PDA), a smart phone, or any programmable electronic device capable of communicating with activity recommendation server 110 via network 102. In another embodiment, target device 104 represents a computing system utilizing clustered computers and components to act as a single pool of seamless resources. In general, target device 104 can be any computing device or a combination of devices with access to activity recommendation server 110, and with access to and/or capable of executing activity recommendation program 300. In some embodiments, a user of target device 104 can input personal physical data and personal activity objectives, link activity tracking devices and weather monitors, and receive activity schedules created by activity recommendation program 300. Target device 104 may include internal and external hardware components, as depicted/described in further detail with respect to FIG. 6.

Target device 104 includes target user interface (UI) 105, which executes locally on target device 104 and operates to provide a UI to a user of target device 104. Target UI 105 further operates to receive user input from a user via the provided user interface, thereby enabling the user to interact with target device 104. In one embodiment, target UI 105 provides a user interface enabling a user of target device 104 to interact with activity recommendation program 300 of activity recommendation server 110 via network 102. In various examples, the user interacts with activity recommendation program 300 in order to input personal physical data and personal activity objectives, link activity tracking devices and weather monitors, and receive activity schedules created by activity recommendation program 300. In one embodiment, target UI 105 is stored target device 104. In other embodiments, target UI 105 is stored on another computing device (e.g., activity recommendation server 110), provided target UI 105 can access and is accessible by target device 104 and activity recommendation program 300.

Activity tracking device 106 is a sensory device capable of monitoring certain physical characteristics. Physical characteristics include monitoring body temperature, heart rate, respiration, physical movement, and brain waves. Activity tracking device 106 monitors and tracks fitness-related metrics such as distance walked or run, calorie consumption, and in some cases, heartbeat and quality of sleep. Activity tracking device 106 may also be capable of monitoring and tracking body temperature, heart rate, brain activity, muscle motion, and sweat rate. In general, activity tracking device 106 tracks movement and rest. In some embodiments, activity tracking device 106 is a computing device, similar to target device 104, capable of communicating with activity recommendation server 110 via network 102. In other embodiments, activity tracking device 106 represents a computing system utilizing clustered computers and components to act as a single pool of seamless resources. In one embodiment, a plurality of activity tracking devices exists, where each activity tracking device monitors physical characteristics and transmits physical activity data to a target device (e.g., target device 104) by activity recommendation program 300. Conventional personal fitness trackers identify many user-specific physical activity data that may be beneficially used by activity recommendation program 300. Additional physical activity data may be collected by other sensors incorporated into fitness trackers or as separate tracking devices. That is, multiple activity tracking devices may be deployed to collect and store physical activity data for use by activity recommendation program 300. In some embodiments, activity tracking device 106 can communicate directly or indirectly with target device 104. Activity tracking device 106 may include internal and external hardware components, as depicted/described in further detail with respect to FIG. 6.

Weather monitor 108 is a device that can send and receive information from an external weather data source in association with a computing device, such as target device 104. In some embodiments, weather monitor 108 obtains weather data associated with one or more external weather data sources. Weather data sources may be personal or commercial weather stations. A user of target device 104 may link weather stations relevant to the user's past locations. Weather data includes weather conditions such as air temperature, cloud coverage, humidity, chance of precipitation, dew point, and pressure. A user of target device 104 may configure weather monitor 108 to collect weather data at certain intervals (i.e. constantly, every 15 minutes, hourly, etc.) In other embodiments, weather monitor 108 may be configured to be a web service that periodically, or as necessary, report weather data or software modules of activity recommendation program 300 that periodically query or interface with various services to obtain the weather data. In some embodiments, weather monitor 108 is a computing device, similar to target device 104, capable of communicating with activity recommendation server 110 via network 102. In other embodiments, weather monitor 108 represents a computing system utilizing clustered computers and components to act as a single pool of seamless resources. In one embodiment, a plurality of weather monitors exists, where each weather monitor monitors the weather surrounding a user of a target device (e.g., target device 104) by activity recommendation program 300. In some embodiments, weather monitor 108 can communicate directly or indirectly with target device 104. Weather monitor 108 may include internal and external hardware components, as depicted/described in further detail with respect to FIG. 6.

Figure 2:
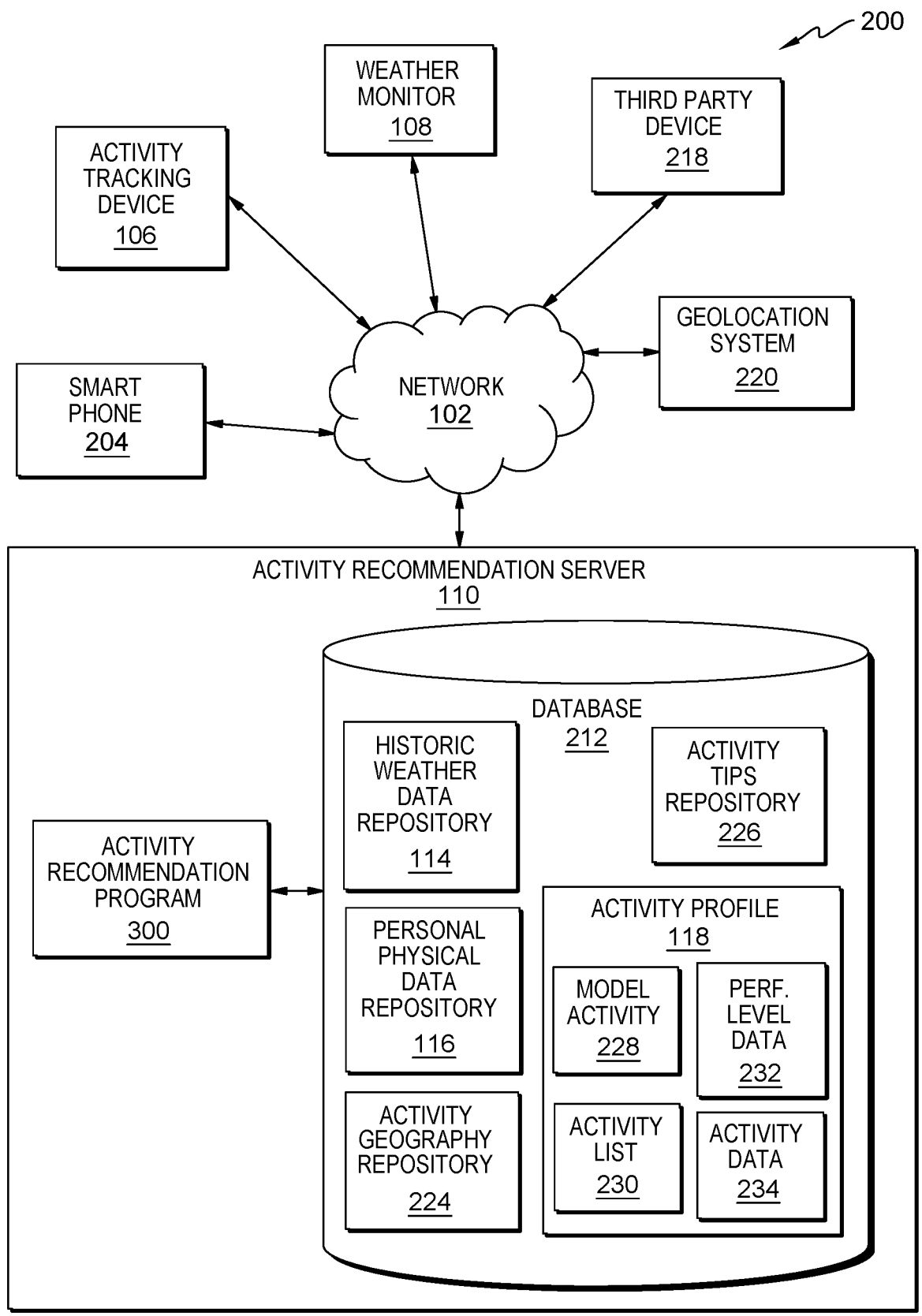
FIG. 2 is a functional block diagram view of a second embodiment of a system according to the present invention.

FIG. 2 is a functional block diagram illustrating a computing environment for scheduling activities for a user based on physical activity data and weather data, in accordance with an embodiment of the present invention. For example, FIG. 2 is a functional block diagram illustrating computing environment 200. Computing environment 200 includes smart phone 204, activity tracking device 106, weather monitor 108, third party device 218, geolocation system 220, and activity recommendation server 110 connected over network 102. Activity recommendation server 110 includes activity recommendation program 300 and database 212. Database 212 includes historic weather data repository 114, personal physical data repository 116, activity profile 118, activity geography repository 224, and activity tips repository 226. Activity profile 118 includes activity model 228, activity list 230, performance level data 232, and activity data 234.

In the specific embodiment depicted in FIG. 2, target device 104 is represented by smart phone 204. As described above with respect to target device 104, smart phone 204 operates as a handheld personal device with a mobile operating system and an integrated mobile broadband cellular network connection for voice, SMS, Internet data, and Wi-Fi communication, capable of communicating with activity recommendation server 110 via network 102 and with access to and/or capable of executing activity recommendation program 300. Smart phone 204 may include internal and external hardware components, as depicted/described in further detail with respect to FIG. 6. In various examples, a user of smart phone 204 interacts with activity recommendation program 300 to input personal physical data and personal activity objectives, link activity tracking devices and weather monitors, and receive activity schedules created by activity recommendation program 300.

Third party device 218 is a computing device, in some embodiments similar to smart phone 204, capable of communicating with activity recommendation server 110 via network 102. In another embodiment, third party device 218 represents a computing system utilizing clustered computers and components to act as a single pool of seamless resources. In general, third party device 218 can be any computing device or a combination of devices with access to activity recommendation server 110, and with access to and/or capable of executing activity recommendation program 300. In one embodiment, a plurality of third party devices exist, where each third party device belongs to third party user submitting physical activity data of the third party user to be utilized by activity recommendation program 300 to develop an activity profile of a user. In some embodiments, third party device 218 can communicate directly or indirectly with smart phone 204. Third party device 218 may include internal and external hardware components, as depicted/described in further detail with respect to FIG. 6.

In general, geolocation system 220 is a system with capabilities to conduct identification or estimation of the real-world geographic location of an object, such as a computing device. Geolocation involves the generation of a set of geographic coordinates and is closely related to the use of positioning systems. In various embodiments, device geolocation can be performed by associating a geographic location with an Internet Protocol (IP) address, a MAC address, RFID tag, a hardware embedded article/production number, an embedded software number, an invoice, a Wi-Fi positioning system, a device fingerprint, canvas fingerprinting, device GPS coordinates, or user-inputted information. Data collected from device geolocation can include information such as country, region, city, postal/zip code, latitude, longitude, and time zone. Deeper data sets can determine other parameters such as domain name, connection speed, ISP, language, proxies, company name, US DMA/MSA, NAICS codes, and home/business. Mobile phone localization, from either multilateration of radio signals between cell towers or by GPS, can also pair a device to a location and a time. The location may be signified as broadly as a zip code or as narrowly as specific longitude/latitude coordinates.

Geolocation system 220 may be a global navigation satellite system that provides geolocation and time information to a GPS receiver anywhere on or near the Earth where there is an unobstructed line of sight to four or more GPS satellites. Geolocation involves the generation of a set of geographic coordinates and is closely related to the use of positioning systems. Device geolocation is performed by associating a geographic location with the GPS coordinates of smart phone 204. Geolocation system 220 can transmit signals to smart phone 204 and/or receive signals from smart phone 204 enabling at least one of, or a combination of, (i) smart phone 204 determining its position based on signal(s) received from geolocation system 220 and (ii) geolocation system 220 determining the location of smart phone 204 based on signal(s) received from smart phone 204. In embodiments utilizing GPS, for example, smart phone 204 transmits and receives signals to and from global navigational satellite systems. In other embodiments utilizing cellular towers, for example, smart phone 204 transmits and receives radio signals between several cellular towers for multilateration. Geolocation system 220 contains a data repository that may be written to and read by geolocation system 220 and stores location information. In general, geolocation system 220 operates to provide geolocation capabilities to smart phone 204 when scheduling nearby locations for activities.

In the specific embodiment depicted in FIG. 2, database 112 is represented by database 212. As described above with respect to database 112, database 212 operates as a data repository that may be written to and read by activity recommendation program 300. Historic weather data, user personal physical data, activity profiles, activity geography data, and activity tips data may be stored to database 212. In some embodiments, database 212 may be written to and read by programs and entities outside of computing environment 200 in order to populate the repository with historic weather data, user personal physical data, activity profiles, activity geography data, and activity tips data. Contents of database 212, including contents of historic weather data repository 114, personal physical data repository 116, activity profile 118, activity geography repository 224, and activity tips repository 226, may be distributed among computing devices in FIG. 2.

Activity profile 118 includes activity model 228, which can be accessed on database 212 by smart phone 204 to be used to recommend activities for a user. Activity model 228 is a physical activity model based on a combination of a physical activity, monitored from activity tracking device 106, and historic weather data defining the prevailing weather conditions during the physical activity, collected from historic weather data repository 114. In some embodiments, activity-specific performance models in activity profile 118 may be updated by a relevant third-party, such as a physician, a teacher, a parent or guardian, a family member or friend of the user, or an employer of the user. Some embodiments of the present invention develop the physical activity model as a table associating user-identified physical activity periods with weather conditions and physical activity data. Using the table, a user may define a desirable physical activity datapoint, or target data point and the activity recommendation program references current weather conditions or forecasted weather conditions of a target date and time to schedule a user-identified activity that has previously recorded the target data point. Alternatively, current weather is monitored by the activity recommendation program and whenever recorded weather conditions are associated with a target data point of the physical activity data, the program prompts the user to engage in the associated user-identified physical activity. Alternatively, physical activity types are pre-defined and determined according to detected physical movement of the user. Further, user-identified physical activity may be user-selected from a pre-defined list of physical activities. It should be note that a physical activity model may be associated with a single user such that a team of users would have a set of physical activity models. The set of physical activity models may be accessed by an activity recommendation program operated by a central server that reports activity schedules to a team leader.

Activity profile 118 includes activity list 230, which can be accessed on database 212 by smart phone 204 to be used to recommend specific activities for a user. Activity list 230 is a repository containing activities that may be scheduled for a user. For example, activity list 230 may contain the following activities: running, weight lifting, hiking, swimming, biking, etc. In some embodiments, a user of smart phone 204 may manually enter and/or update activities to activity list 230. In other embodiments, activities may be entered and/or updated into activity list 230 from a relevant third-party, such as a physician, a teacher, a parent or guardian, a family member or friend of the user, or an employer of the user. In some embodiments, activity recommendation program 300 updates activity list 230 based on the activities entered by a user while utilizing activity recommendation program 300.

Activity profile 118 includes performance level data 232, which can be accessed on database 212 by smart phone 204 to be used to schedule physical activities for a user. Performance level data 232 is a repository containing performance level data for physical activities performed by a user. The performance level may be derived from the set of physical activity data obtained during the period in which the physical activity is performed. Alternatively, the performance level is self-assessed at the end of the physical activity period is completed.

Activity profile 118 includes activity data 234, which can be accessed on database 212 by smart phone 204 and stores physical activity data collected by an activity tracking device, such as activity tracking device 106. Physical activity data may include body temperature, heart rate, respiration, physical movement, muscle motion, and brain waves collected while a user is conducting an activity. Physical activity data may also include fitness-related metrics such as distance walked or run, calorie consumption, heartbeat, sweat rate, and quality of sleep/rest. In some embodiments, advanced or "smart" activity tracking devices are implemented that can track other metrics associated with specific activities. For example, an activity tracking device specialized for swimmers can track swimming metrics such as swimming stroke count, pace, time, interval, calories burned, stroke type, heart rate, and oxygen output.

Database 212 includes activity geography repository 224, which can be accessed on database 212 by smart phone 204 to utilize location information related to possible activities for a user. Activity geography repository 224 may contain activity location information pertaining to activities geographically close to a user. For example, for a runner, activity geography repository 224 may contain running routes that are close to the runner. In some embodiments, a user of smart phone 204 may manually enter and/or update activity location data to activity geography repository 224.

In other embodiments, activity location data may be entered and/or updated into activity geography repository 224 from a relevant third-party, such as a physician, a teacher, a parent or guardian, a family member or friend of the user, or an employer of the user.

Database 212 includes activity tips repository 226, which can be accessed on database 212 by smart phone 204 to utilize activity tips information when generating scheduled activities for a user. Activity tips repository 226 may contain tips pertaining to activities. For example, for a runner, activity tips repository 226 may contain the tip "consider bringing a light coat" when scheduling an activity outside when the air temperature is cold. In some embodiments, a user of smart phone 204 may manually enter and/or update activity tips data to activity tips repository 226. In other embodiments, activity tips data may be entered and/or updated into activity tips repository 226 from a relevant third-party, such as a physician, a teacher, a parent or guardian, a family member or friend of the user, or an employer of the user.

Figure 3:
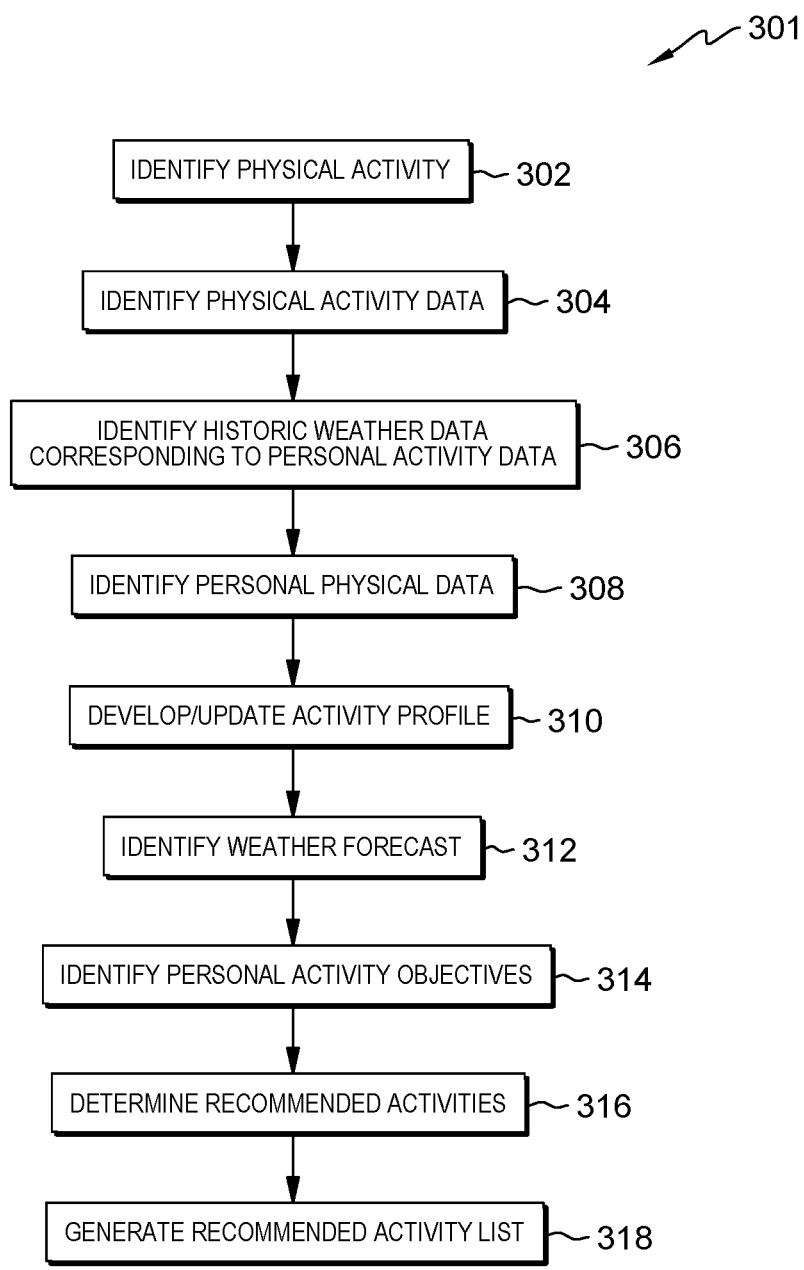
FIG. 3 is a flowchart showing a method performed, at least in part, by the first or second embodiment system.

FIG. 3 is a flowchart depicting operations for scheduling activities for a user based on physical activity and weather, on a computing device within the computing environments of FIGS. 1 and 2, in accordance with an embodiment of the present invention. For example, FIG. 3 is a flowchart depicting operations 301 of activity recommendation program 300 on activity recommendation server 110 within computing environments 100 and 200. In other examples, FIG. 3 is a flowchart depicting operations of activity recommendation program 300 on target device 104 within computing environment 100. In yet other examples, FIG. 3 is a flowchart depicting operations of activity recommendation program 300 on smart phone 204 within computing environment 200. In different embodiments, there are multiple variations of the order of the steps that may be applied. For example, in some embodiments, the order in which data is identified may differ from the embodiment depicted in FIG. 3.

Activity recommendation program 300 identifies a physical activity of a user (step 302). Physical activities are discretely identified as taking place over a particular period of time. In that way, weather data may be associated with particular activities. In this example, activity list 230 of FIG. 2 includes identifiable physical activities. Alternatively, when a user participates in a physical activity, a name of the activity is entered by the user into an activity list. For example, a user who is going skiing may input the activity "skiing" as a current activity for monitoring by activity recommendation program 300. With this input, activity recommendation program 300 identifies skiing as the current activity. In other embodiments, activity recommendation program 300 utilizes information collected from an activity tracking device, such as activity tracking device 106, to determine the activity. Certain activity tracking devices may determine an activity based on the specific physical movements of a user typically associated with the activity. For example, a user utilizes one or more activity tracking devices that can track physical movement while the user skis. Based on the tracked physical movements, such as specific arm and/or leg movement, activity recommendation program 300 determines the activity is skiing.

Activity recommendation program 300 identifies physical activity data for a user (step 304). Physical activity data includes data collected from an activity tracking device, such as activity tracking device 106 of FIG. 2. Many commercial activity tracking devices have application programming interfaces to access data. Physical activity data may include body temperature, heart rate, respiration, physical movement, muscle motion, and brain waves collected while a user is performing an activity. Physical activity data may include fitness-related metrics such as distance walked or run, calorie consumption, heartbeat, sweat rate, and quality of sleep/rest. In some embodiments, advanced or "smart" activity tracking devices are deployed for collecting metrics associated with specific activities. For example, an activity tracking device specialized for swimmers tracks specific swimming metrics such as swimming stroke count, pace, time, interval, calories burned, stroke type, heart rate, and/or oxygen output.

An activity tracking device may directly transmit physical activity data to a smart device of a user, such as smart phone 204, or to activity recommendation server 110, or specifically to a database, such as database 212, for storage. In some embodiments, a user, using a user interface of a smart device, can configure activity recommendation program 300 to track physical activity at specific dates/times, such as when a physical activity is taking place. In other embodiments, the user may configure activity recommendation program 300 to track physical activity at all times, wherein the activity tracking device and/or activity recommendation program 300 differentiates when a physical activity is taking place. Activity recommendation program 300, in conjunction with a smart device, may utilize GPS capabilities and past activity history, found in database 212, to determine when a specific activity took place during a timeline while the user utilizes the activity tracking device. For example, if a user wears a wrist-based activity tracking device over a period of 24 hours, activity recommendation program 300 may identify physical activity data during the time within the 24 hours that the user participated in activities.

Activity recommendation program 300 identifies historic weather data corresponding to identified physical activity data (step 306). Historic weather data includes data accessed on a repository on a database by a user's device, such as historic weather data repository 114 located on database 212 and accessed by smart phone 204 of FIG. 2. Historic weather data, identified by activity recommendation program 300, may originate from one or more external weather data sources. Weather data sources may be personal or commercial weather stations. A user of smart phone 204 may link weather stations relevant to the user's past locations. For example, a user participates in activities in Location A and Location B. The user links weather stations relevant to Location A and Location B. Historic weather data includes weather conditions such as air temperature, cloud coverage, humidity, precipitation, dew point, and pressure. Activity recommendation program 300 identifies the weather conditions during which the user participates in an activity. For example, if a user ran two miles last week, activity recommendation program 300 identifies the air temperature, cloud coverage, humidity, and other weather conditions while the user was on the two-mile run. A user of smart phone 204 may configure activity recommendation program 300 to identify weather conditions at certain intervals (i.e. constantly, every 15 minutes, hourly, etc.) during the activity. In some embodiments, a user, using a user interface of a smart device, can configure activity recommendation program 300 to identify historic weather data at specific dates/times, such as when a physical activity is taking place. In other embodiments, the user may configure activity recommendation program 300 to identify historic weather data when an activity tracking device, such as activity tracking device 106, is being used by a user.

Activity recommendation program 300 identifies personal physical data associated with a user (step 308). Personal physical data includes data accessed on a repository on a database by a user's device, such as personal physical data repository 116 located on database 212 and accessed by smart phone 204 of FIG. 2. Personal physical data includes age, height, weight, and gender of a user. In some embodiments, a user, using a user interface of a smart device, can input and/or update personal physical data stored in personal physical data repository 116. In other embodiments, certain types of personal physical data, such as weight, may be inputted into personal physical data repository 116 when a user utilizes a network-connected weighing scale. In some embodiments, a user of smart phone 204 may manually enter and/or update personal physical data. In other embodiments, personal physical data may be entered and/or updated to activity recommendation program 300 from a relevant third-party, such as a physician, a teacher, a parent or guardian, a family member or friend of the user, or an employer of the user.

Activity recommendation program 300 develops/updates an activity profile of a user (step 310). The activity profile includes a physical activity model associating physical activity performance levels of a user with prevailing weather conditions when the physical activity is performed. The activity profile, particularly the physical activity model, serves to guide a determination of how a set of weather conditions will affect the performance level of a specified physical activity when performed by a particular user. That is, for a given user, the unique physical response to the weather is documented in such a way that user-specific guidance is available for what physical activities are best performed by the specific user during a particular set of weather conditions. Over time, the activity profile will contain numerous data points for individual performance of physical activities. In that way, the physical activity model is continually updated to more precisely identify physical activities to be performed by the user during particular weather conditions. The activity profile may be stored on a database, such as database 212. The activity profile model may be used to recommend activities for a user.

Some embodiments of the present invention apply a collaborative filtering approach to establish a starting point for physical activity performance levels based on a personal physical data. In this case, third party users of activity recommendation programs with similar personal physical data characteristics (such as similar age, height, weight, etc.) may agree to share their physical activity profile data as a baseline to launch a new user. Alternatively, a pool of users who share their physical activity profile data to establish baseline profiles for new users. As a new user provides physical activity data the baseline profile data is replaced such that a hybrid profile is created. A hybrid activity profile uses collaborative filtering and user-specific context-based filtering to develop a physical activity model for the user.

Collaborative filtering refines schedules based on similar users. Collaborative filtering is a scheduling system that seeks to predict a preference a user would give to certain things, such as activities. Collaborative filtering methods are based on collecting and analyzing a large amount of information on users' behaviors, activities, or preferences, and predicting what users will like based on their similarity to other users. Activity recommendation program 300 utilizes collaborative filtering by (i) searching for users of activity recommendation program 300 who share similar personal physical data with a user of a smart device, such as smart phone 204, and (ii) use the activities that those similar users have preferred to calculate a prediction for the user of the smart device.

Collaborative filtering may be memory-based or model-based. The memory-based approach uses user rating data to compute the similarity between user. Similar users to the user of the smart device may be calculated by using one of a number of similarity or distance metrics, such as cosine similarity or Euclidean distance. In some embodiments, other memory-based collaborative filtering algorithms may be used. The model-based approach uses machine learning algorithms and pattern recognition techniques to predict user ratings of activities. Machine learning explores the study and construction of algorithms that can learn from and make predictions based on data. Such algorithms operate by building a model from example inputs in order to make data-driven predictions or decisions expressed as outputs, rather than following strictly static program instructions.

Within the field of data analytics, machine learning is a method used to devise complex models and algorithms that lend themselves to decisions, and probability related prediction. These analytical models enable researchers, data scientists, engineers, and analysts to produce reliable, repeatable decisions and results and to uncover hidden insights through learning from historical relationships and trends in the data. Pattern recognition is a branch of machine learning that focuses on the recognition of patterns and regularities in data. Pattern recognition systems may be trained from labeled "training" data (supervised learning), but when no labeled data are available, other algorithms can be used to discover previously unknown patterns (unsupervised learning). Activities conducted by users with similar personal physical data may represent training data for supervised learning.

Context-based filtering does not need information from other users and is personalized based on activity performance levels of a user for certain physical activities and activity objectives of the user. Context-based filtering can rank schedules that include similar, but unused, activities a user prefers. For example, a new running path may be scheduled that is popular in a runner's area. Context-based filtering methods are based on a description of an item and a profile of the user's preferences. In a context-based scheduling system, keywords are used to describe the items and a user profile is built to indicate the type of item this user likes. In other words, these algorithms identify items that are similar to those that a user liked in the past. In particular, various candidate items are compared with items previously rated by the user and the best-matching items are scheduled.

To abstract the features of the items in the system, an item presentation algorithm is applied. To create an activity profile, the activity recommendation program 300 mostly focuses on two types of information: (i) A model of the user's preference and (ii) A history of the user's interaction with the scheduling system. These methods use an activity profile (i.e., a set of discrete attributes and features) characterizing the activity within the system. The system creates a context-based profile of a user based on a weighted vector of activity features. The weights denote the importance of each feature to the user and can be computed from individually rated context vectors using a variety of techniques. Simple approaches use the average values of the rated activity vector, while other sophisticated methods use machine learning techniques such as Bayesian classifiers, cluster analysis, decision trees, and artificial neural networks in order to estimate the probability that the user is going to like the activity.

A hybrid approach that uses collaborative filtering and context-based filtering may be used by activity recommendation program 300 to develop an activity profile model.

Hybrid approaches can be implemented in several ways: by making context-based and collaborative-based predictions separately and then combining them; by adding context-based capabilities to a collaborative-based approach (and vice versa); or by unifying the approaches into one model. Physical activity data and historic weather data are used by activity recommendation program 300 as variables to create an activity profile model. The hybrid approach analyzes these two variables using machine learning and pattern matching techniques to predict optimal activity performance conditions. In an exemplary embodiment, activity recommendation program 300 analyzes a runner's physical activity data and the historic weather data corresponding to the physical activity data. Hybrid filtering develops a model that predicts the average speed changes with outdoor air temperature. Specifically, activity recommendation program 300 determines that for within an air temperature range of 15° C. and 26° C., the average running speed increases by 0.2 km/hour for each 1° C. the air temperature decreases. Based on this correlation model, activity recommendation program 300 develops an activity profile for the runner.

In some embodiments, the activity profile is updated by activity recommendation program 300 after each activity performed by a user. Machine learning methods may be utilized by activity recommendation program 300 to update the model of an activity profile. In one embodiment, an online machine learning algorithm is used. online machine learning is a method of machine learning in which data becomes available in a sequential order and is used to update the best predictor for future data at each step, as opposed to batch learning techniques which generate the best predictor by learning on the entire training data set at once. Online learning is a common technique used in areas of machine learning where it is computationally infeasible to train over the entire dataset, requiring the need of out-of-core algorithms. It is also used in situations where it is necessary for the algorithm to dynamically adapt to new patterns in the data, or when the data itself is generated as a function of time. For activity recommendation program 300, a user's activity profile can be updated after an activity is performed by the user.

Activity recommendation program 300 identifies the weather forecast over a period of time (step 312). In some embodiments, a user, using a user interface of a smart device, can configure activity recommendation program 300 to identify the weather forecast for a given number of days in the future. For example, a user may configure activity recommendation program 300 to identify the weather forecast for the user's location for the next seven days. Due to the nature of weather forecasting, identified weather forecasts for days farther from the present tend to be less accurate than identified weather forecasts for days closer to the present. In other embodiments, a user, using a user interface of a smart device, can configure activity recommendation program 300 to identify the weather forecast for a given location. Activity recommendation program 300 may utilize a geolocation system, such as geolocation system 220 of FIG. 2, for more accurate location-based weather forecasting. A weather forecast includes data collected from a weather monitor, such as weather monitor 108. Weather forecasts, identified by activity recommendation program 300, may originate from one or more external weather data sources. Weather data sources may be personal or commercial weather stations. In some embodiments, a user of smart phone 204 can link weather stations relevant to the user's past locations. For example, a user normally participates in activities in Location A and Location B. The user links weather stations relevant to Location A and Location B. Weather forecasts include weather condition data such as air temperature, cloud coverage, humidity, precipitation, dew point, and pressure.

Activity recommendation program 300 identifies personal activity objectives for a user (step 314). In some embodiments, a user, using a user interface of a smart device, can input personal activity objectives for activity recommendation program 300. Personal activity objectives may consist of broad or narrow activity preferences, activity schedules, and/or performance limitations. For example, a runner training for a marathon uses a running schedule that requires the user to engage in runs of various specified distances five times per week for several weeks. The runner may input a marathon training schedule into activity recommendation program 300 as their personal activity objectives. The runner may further request running activity schedules for a five-day period during the next week.

In another example, a user rehabilitating an injured arm may input to activity recommendation program 300 a preference for activities that do not strain arms. In some embodiments, a user of smart phone 204 may manually enter and/or update personal activity objectives. In other embodiments, personal activity objectives may be entered and/or updated to activity recommendation program 300 from a relevant third-party, such as a physician, a teacher, a parent or guardian, a family member or friend of the user, or an employer of the user.

Some embodiments of the present invention prepare a physical activity schedule drawing from user-specified activities and previously recorded performance levels achieved by the user performing the user-specified activities during weather conditions similar to current or forecast weather conditions. Further, some embodiments of the present invention prompt a user to perform according to the physical activity schedule when current conditions match the forecasted conditions used to prepare the schedule. Alternatively, when current conditions do not match forecast conditions, the physical activity schedule is updated to postpone physical activities or modify the scheduled physical activity to a user-specified activity better suited for the user to perform during the current weather conditions. It should be noted that a "user-specified activity" as used herein may be specified by a physician, caretaker, or manager responsible for assigning particular physical activities to the user.

Activity recommendation program 300 determines activities to schedule for a user (step 316). In general, activity recommendation program 300 determines activities based on a combination of an activity profile of a user, developed by activity recommendation program 300 and stored on a database, such as activity profile 118 on database 212 of FIG. 2, weather forecast data, monitored from a weather monitor, such as weather monitor 108, and personal activity objectives inputted by the user. The determined activities to schedule for a user may be stored on a database, such as database 212. The activities are activities determined by activity recommendation program 300 are scheduled such that the top options that generate the optimal activity performance for a user are scheduled.

In some embodiments, activity recommendation program 300 utilizes a hybrid approach that uses collaborative filtering and context-based filtering to determine activities for a user. Collaborative filtering and context-based filtering are previously described in step 310. Collaborative filtering refines the activity schedule based on similar users. In some embodiments, one or more third party devices exist, such as third party device 218, with users of third party devices using activity recommendation program 300. In this case, third party users of activity recommendation program 300 with similar personal physical data characteristics (such as similar age, height, weight, etc.) are used as similar users.

Activity recommendation program 300 may utilize collaborative filtering by (i) searching for users of activity recommendation program 300 who share similar personal physical data with a user of a smart device, such as smart phone 204, and (ii) using the activities that those similar users have preferred to calculate a prediction for the user of the smart device. Context-based filtering does not need information from other users and is personalized based on activity performance levels and/or personal objectives. Context-based filtering can rank schedules that include similar but unused activities to other activities a user prefers. For example, a new running path may be scheduled that is popular in a runner's area. Hybrid approaches can be implemented in several ways: by making context-based and collaborative-based predictions separately and then combining them; by adding context-based capabilities to a collaborative-based approach (and vice versa); or by unifying the approaches into one model. In some embodiments, hybrid approach utilized by activity recommendation program 300 uses the activity profile, weather forecast data, and activity objectives as variables using machine learning and pattern matching techniques to predict optimal activity performance conditions.

Potential schedule algorithms utilized by activity recommendation program 300 include matrix factorization, classification methods, clustering methods, and optimization methods. Matrix factorization algorithms work by decomposing the user-item interaction matrix into the product of two lower dimensionality rectangular matrices. Matrix factorization may utilize linear algebra concepts such as singular value decomposition and statistical procedures such as principal component analysis. Classification methods (or statistical classification) may utilize machine learning concepts with statistical concepts such as logistic regression and decision trees. Clustering methods may utilize machine learning concepts with statistical algorithms such as k-means clustering and density-based spatial clustering of applications with noise (DBSCAN). Optimization methods (or mathematical optimization) may utilize statistical concepts such as Markov chains.

In some embodiments, activity recommendation program 300 schedules multiple options for activities for a user throughout the day or week. These options may be differing routes and times for an activity. For example, activity recommendation program 300 schedules a user to go for a two mile run on the following Monday. Activity recommendation program 300 may schedule different start times and/or different routes for the user. Activity recommendation program 300 may utilize machine learning decision making algorithms to generate activity schedules if a user configures activity recommendation program 300 to allow for multiple options.

Continuing the exemplary embodiment described in step 310, based on the activity profile developed by activity recommendation program 300 for the runner, activity recommendation program 300 determines activity schedules that optimize running performance levels for the runner. Activity recommendation program 300 determines activity schedules for the runner as runs that occur in air temperatures around 15° C. Since those air temperatures typically occur during the morning or night in that particular area, activity recommendation program 300 determines activity schedules for the runner during the morning or night.

Activity recommendation program 300 generates a list of activities for a user (step 318). In some embodiments, a user can view an activity schedule generated by activity recommendation program 300 on a smart device, such as smart phone 204 of FIG. 2. The activity schedule may be presented in various ways for a user. For example, the activity schedule may be presented as an ordered list of activities. The list may be ranked by activity recommendation program 300 by how likely a user participates in the activity with optimal performance.

In some embodiments, activity recommendation program 300 utilizes location information related to physical activities to display geographical routes for a user. Activity recommendation program 300 may utilize activity location information pertaining to activities geographically close to a user. Activity location information may include GPS coordinates associated with a particular activity which can be used to display the activity on a map for a user. For example, activity recommendation program 300 schedules running outside for a certain distance to a user. Activity recommendation program 300 may display running routes on a map for a user based on GPS coordinates of running routes stored as activity location information. This may be convenient for a user viewing the displayed map, as the user may be able to plan to participate in the scheduled activity based on the running route.

Activity recommendation program 300 may access activity location information from a repository such as activity geography repository 224 on database 212. In other embodiments, activity recommendation program 300 displays tips regarding scheduled activities. Tips may include helpful information regarding the activity based on the geography of the activity, the weather, or other things associated with the activity. For example, activity recommendation program 300 schedules running outside to a user. The air temperature outside is slightly cold. Activity recommendation program 300 may display a tip such as "consider bringing a light coat" to the user. Activity recommendation program 300 may access activity tips information from a repository such as activity tips repository 226 on database 212.

Figure 4A:
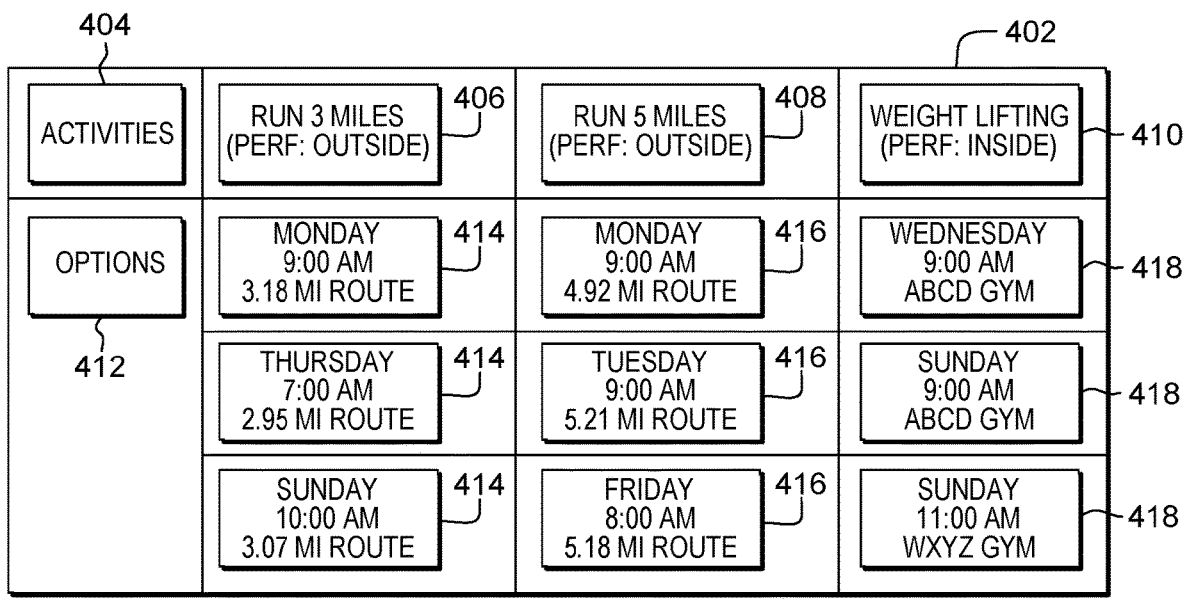
FIG. 4A is a screenshot view showing information that is generated by and/or helpful in understanding embodiments of the present invention.
Figure 4B:
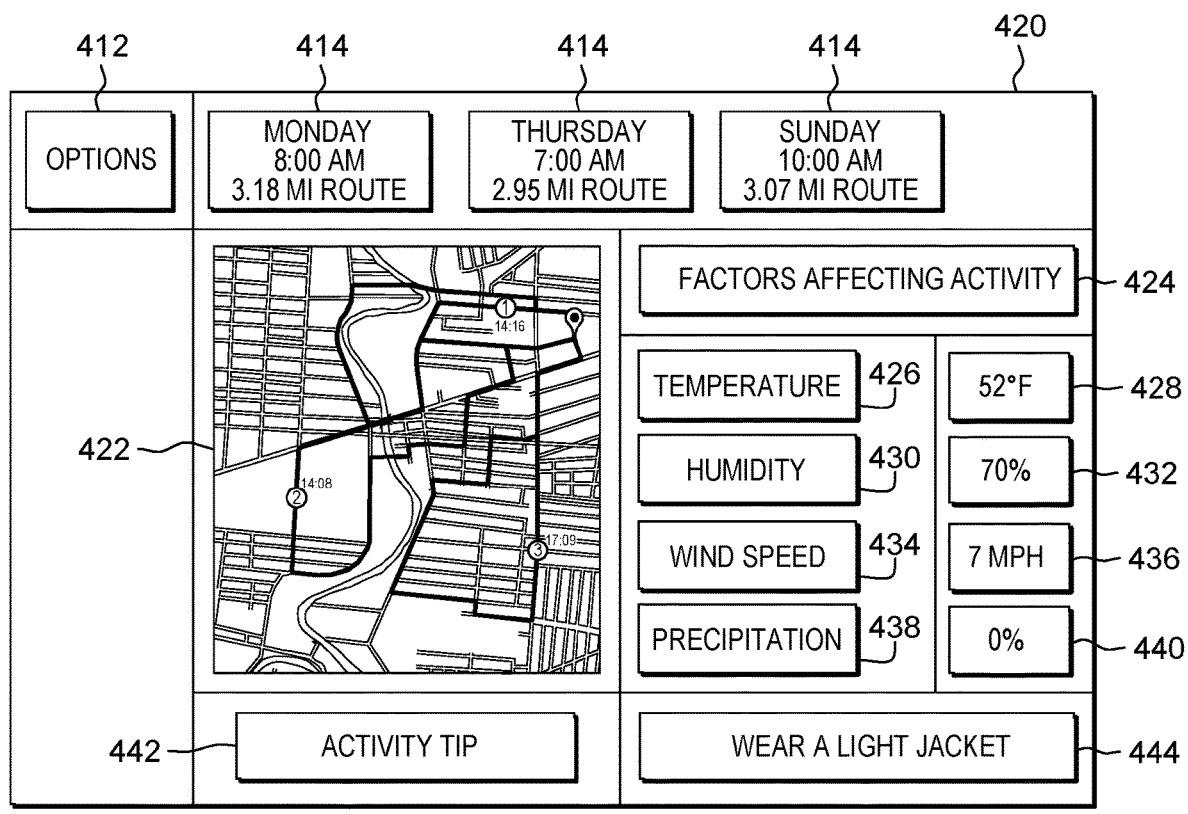
FIG. 4B is a screenshot view showing information that is generated by and/or helpful in understanding embodiments of the present invention.

FIGS. 4A and 4B are screenshots of example interactive generated activity lists displayed by a computing device within the computing environment of FIG. 1 and/or FIG. 2, in accordance with an embodiment of the present invention. For example, FIGS. 4A and 4B depict screenshots 402 and 420, associated with activity recommendation program 300 on activity recommendation server 110 within computing environment 100 and/or computing environment 200. In other examples, FIGS. 4A and 4B depict screenshots 402 and 420, associated with activity recommendation program 300 on target device 104 within computing environment 100 and/or smart phone 204 within computing environment 200.

FIG. 4A depicts screenshot 402 of an example interactive generated activity list, in accordance to an embodiment. Screenshot 402 includes activities label display 404, determined activity display 406, determined activity display 408, determined activity display 410, options label display 412, activity option display 414, activity option display 416, and activity option display 418. Activities label display 404 displays the label "ACTIVITIES." The determined activities follow to the right of activities label display 404. Determined activity display 406 displays an example activity. In this example, the activity is "RUN 3 MILES (PREF: OUTSIDE)." Determined activity display 408 displays an example activity. In this example, the activity is "RUN 5

MILES (PREF: OUTSIDE)." Determined activity display 410 displays an example activity. In this example, the activity is "WEIGHT LIFTING (PREF: INSIDE)." Options label display 412 displays the label "OPTIONS." The activity options corresponding to the activities follow to the right of options label display 412. Activity option display 414 displays three example activity options corresponding to the activity of determined activity display 406. Activity option display 416 displays three example activity options corresponding to the activity of determined activity display 408. Activity option display 418 displays three example activity options corresponding to the activity of determined activity display 410.

FIG. 4B depicts screenshot 420 of an example interactive generated activity list, in accordance to an embodiment. Screenshot 420 includes options label display 412 and activity option display 414, previously described in FIG. 4A. Screenshot 420 also includes map display 422, factors label display 424, temperature label display 426, temperature display 428, humidity label display 430, humidity display 432, wind speed label display 434, wind speed display 436, precipitation label display 438, precipitation display 440, tip label display 442, and tip display 444. Map display 422 displays a map of routes for activity options displayed in activity option display 414. Factors label display 424 displays the label "FACTORS AFFECTING ACTIVITY." The factors affecting the activity follow under factors label display 424. Temperature label display 426 displays the label "TEMPERATURE." Temperature display 428 displays the air temperature associated with the activity. Humidity label display 430 displays the label "HUMIDITY." Humidity display 432 displays the humidity associated with the activity. Wind speed label display 434 displays the label "WIND SPEED." Wind speed display 436 displays the wind speed associated with the activity. Precipitation label display 438 displays the label "PRECIPITATION." Precipitation display 440 displays the chance of precipitation associated with the activity. Tip label display 442 displays the label "ACTIVITY TIP." Activity tips corresponding to the determined activity follow to the right of tip label display 442. Tip display 444 displays a tip associated with the activity.

To illustrate the functionality described above with respect to FIGS. 2, 3, 4A, and 4B, in one specific example, a user, Abel, is an athlete that utilizes activity recommendation program 300 with a smart phone device. Abel desires activity schedules for the next seven days. Abel wears a physical activity tracker. During every physical activity, activity recommendation program 300 identifies physical characteristic data on Abel via the physical activity tracker. Physical characteristic data identified by activity recommendation program 300 includes body temperature, heart rate, respiration, distance ran, and run speed.

Activity recommendation program 300 identifies historic weather data associated with every run performed by Abel via a historic weather data repository. Historic weather data identified by activity recommendation program 300 includes air temperature, humidity, wind speed, and precipitation. Using the smart phone, Abel inputs personal physical data to be identified by activity recommendation program 300. Personal physical data inputted by Abel includes Abel's age, height, and weight. Using activity information from other users of activity recommendation program 300 with similar ages, heights, and/or weights as Abel and activity/weather information of Abel's past activities, activity recommendation program 300 develops an activity profile for Abel.

The activity profile includes an activity profile model for use by activity recommendation program 300 to determine activities for scheduling. Activity recommendation program 300 identifies weather forecasts for the next seven days for the geographic area of Abel. Specifically, activity recommendation program 300 identifies air temperature, humidity, wind speed, and precipitation forecasts. Using the smart phone, Abel inputs personal activity objectives to be identified by activity recommendation program 300. Abel's personal activity objectives include preferences to run outdoors twice during the week and participate in weight lifting indoors once during the week. Abel also inputs a preference to participate in physical activities during the morning. Using the activity profile developed by activity recommendation program 300, the weather forecast for the week, and Abel's personal activity objectives, activity recommendation program 300 determines activity schedules. Activity recommendation program 300 generates an interactive list of activity schedules for Abel, as depicted in FIGS. 4A and 4B.

As depicted in FIG. 4A, activity recommendation program 300 determines three activities for Abel, running 3 miles (determined activity display 406), running 5 miles (determined activity display 408), and weight lifting (determined activity display 410). Activity recommendation program 300 displays multiple options for each activity schedule, as depicted as activity option display 414, activity option display 416, and activity option display 418. As depicted in FIG. 4B, activity recommendation program 300 displays route options for the running 3 miles activity (activity option display 414). Activity recommendation program 300 displays the running routes for the three route options on a map, as depicted by map display 422. Activity recommendation program 300 displays the factors affecting activity, with the forecasted air temperature of 52° F. (temperature display 428), humidity of 70% (humidity display 432), wind speed of 7 mph (wind speed display 436), and chance of precipitation of 0% (precipitation display 440). Activity recommendation program 300 displays an activity tip for the activity. Activity recommendation program 300 displays "wear a light jacket" as depicted by tip display 444.

Figure 5:
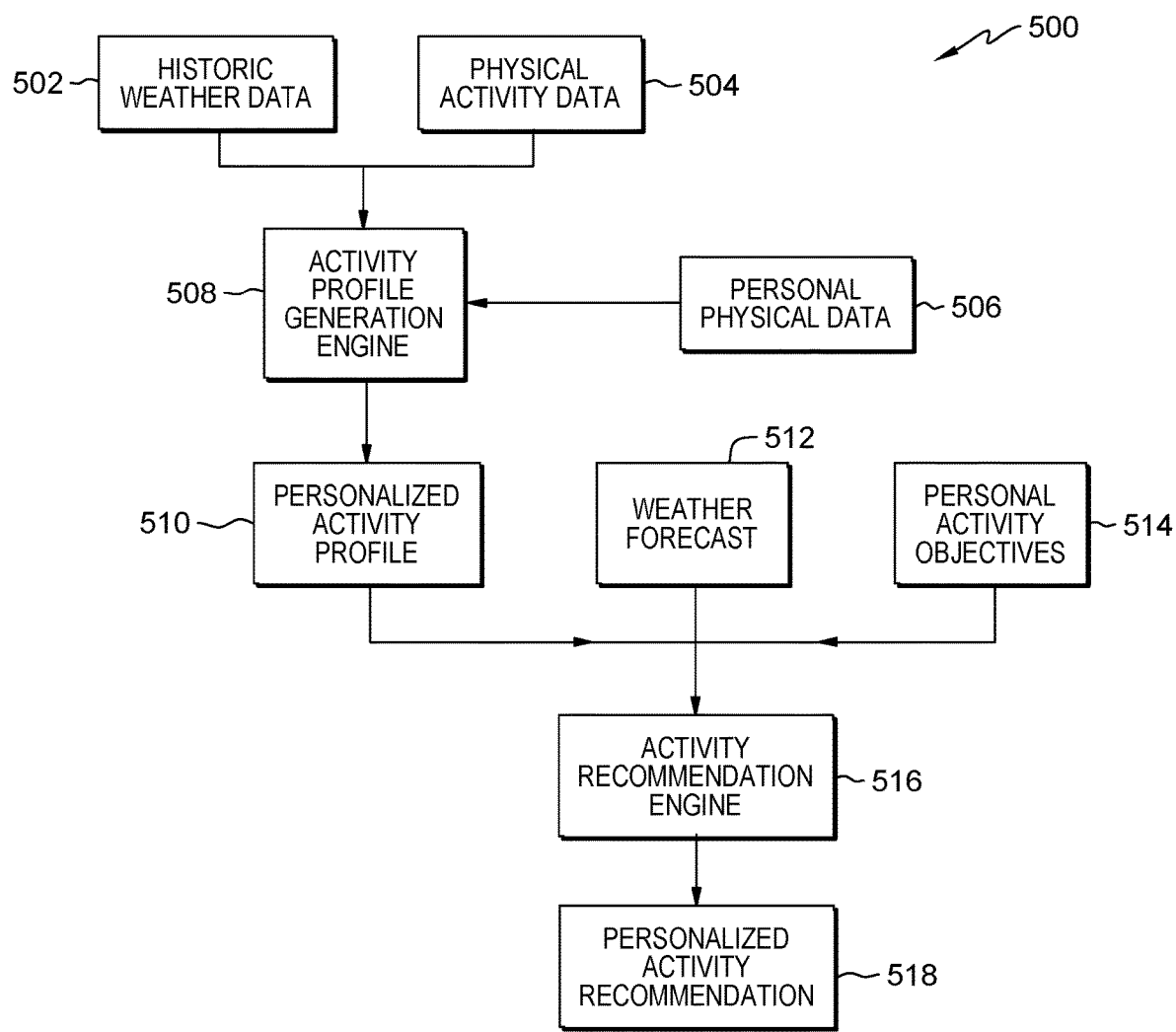
FIG. 5 is a schematic view of a flowchart showing a method performed according to embodiments of the present invention.

FIG. 5 is a schematic view of computer system 500, illustrating a computing environment for physical activities for a user based on physical activity data and weather data, in accordance with an embodiment of the present invention. In this embodiment, activity profile engine 508 and activity recommendation engine 516 functions in a similar role as discussed with respect to activity recommendation program 300.

The method begins concurrently with historic weather data 502, physical activity data 504, and personal physical data 506. Historic weather data 502, physical activity data 504, and personal physical data 506 are utilized by activity profile generation engine 508. Physical activity data of physical activity data 504 is user data gathered from an activity tracking device. Personal physical data of personal physical data 506 is personal physical data entered by a user of activity recommendation program 300. Activity profile generation engine 508 generates personalized activity profile 510. An initial personalized activity profile is generated based on physical activity data, personal physical data, and historic weather data. Personalized activity profile 510, weather forecast 512, and personal activity objectives 514 are utilized by activity recommendation engine 516. Personal activity objectives of personal activity objectives 514 may be for a given time frame as configured by a user of activity recommendation program 300. Activity recommendation engine 516 generates personalized activity recommendation 518. All analysis may be performed in cloud to take processing load off a local device, such as an activity tracking device or smart phone.

Embodiments of the present invention recognize that for some people, returning to healthy activity after surgery or an injury can be difficult. People often start an exercise regime with enthusiasm but do not continue the regime after a period of time. Health care providers give occasional guidance and encouragement, but this may be limited to clinic visits. Weather can aggravate or add to a pre-existing condition. For example, heat strokes or increased risk of slipping on wet or icy pavement may result in medical problems for people. Some people may injure themselves by pushing too hard initially with physical activity. Some people may also get bored or frustrated after not seeing desired physical results quickly enough. Activity recommendation program 300 may utilize weather data, performance levels on previous physical activities, and a recommended activity schedule, to provide a patient with customized physical activity schedules on a regular basis. This may reduce chance of injury and boredom, while also increasing chances that patient stays active. This may also remind patients when to start exercising.

Embodiments of the present invention recognize weather conditions can affect both the timeliness of a construction project and the health of construction workers. Extreme weather conditions may impact the health of construction workers completing certain construction tasks. Weather can also impact the timeliness of construction products and when different tasks (such as painting, pouring concrete, laying brick, etc.) can occur. Activity recommendation program 300 may utilize the weather forecast, performance levels on previous construction tasks (such as heart rate, body temperature, etc.), and the recommended construction schedule to determine which days are the best for a worker to complete various construction tasks across the construction site or sites if a company is managing multiple projects. This may reduce the chance of injury or health problem from construction tasks. This may also improve timeliness of construction project, especially for a large company managing several projects.

For example, employees work for a construction company where the primary tasks for the employees are painting, bricklaying, welding, and wiring. Each employee may be tracked by an activity tracking device. Activity recommendation program 300 may utilize weather conditions and employee's physical history to calculate a consistency metric for a given day, where the consistency metric measures how efficiently the employee conducts a task on that day. This consistency metric may be used as an activity profile for the employees. Activity recommendation program 300 may determine a schedule for the employees based on employee consistency metrics and the weather forecast for the week. In an example, activity recommendation program 300 schedules employee Baker to paint on Monday, brick lay on Tuesday, weld on Wednesday, and wire on Thursday, due to the varying air temperature, chance of rain, and humidity throughout the week. Activity recommendation program 300 may also provide helpful tips to the employees based on the weather conditions on a specific day. Activity recommendation program 300 suggests Baker consider dressing in layers on Wednesday because of the cold weather.

Some embodiments of the present invention are directed to generating a schedule for performance of a physical activity by (i) monitoring a physical activity performed by a user wearing an activity tracker during a period of time; (ii) receiving activity data from the activity tracker, the activity tracker tracking physical movement of the user during the period of time; (iii) determining environmental data in which the physical activity occurs for the period of time; (iv) receiving physical data describing physical conditions of the user while performing the physical activity; (v) generating a physical activity model that correlates the activity data, the environmental data, and the physical data chronologically over the period of time; (vi) identifying a weather forecast for a geographic region in which the user will be located at a specified time range; (vii) determining, for the specified time range, a set of physical activities for the user to perform including the physical activity; and (viii) generating a schedule for user to perform the physical activity during the specified period of time, the schedule being determined by the physical activity model according to the weather forecast.

Some embodiments of the present invention further include one or more of the following steps, conditions, or limitations: (i) identifying the physical activity from a table of potential activities and corresponding physical movement associated with the physical activity; (ii) the schedule includes a activity period for performing the physical activity within the specified time range; (iii) determining a performance level during the period of time, the performance level indicating a degree of efficiency in performing the physical activity according to the activity data and the physical data; (iv) associating the performance level with the physical activity in the physical activity model; (v) determining a desired performance level for the physical activity; (vi) the physical activity model requires a predicted performance level during the schedule to be at least as high as the desired performance level; (vii) determining the physical activity is being performed during a second period of time; (viii) receiving additional activity data from the activity tracker during the second period of time; (ix) determining additional environmental data during the second period of time; (x) receiving additional physical data during the second period of time; and/or (xi) responsive to the end of the second period of time, revising the physical activity model correlate the additional activity data, the additional environmental data, and the additional physical data.

Figure 6:
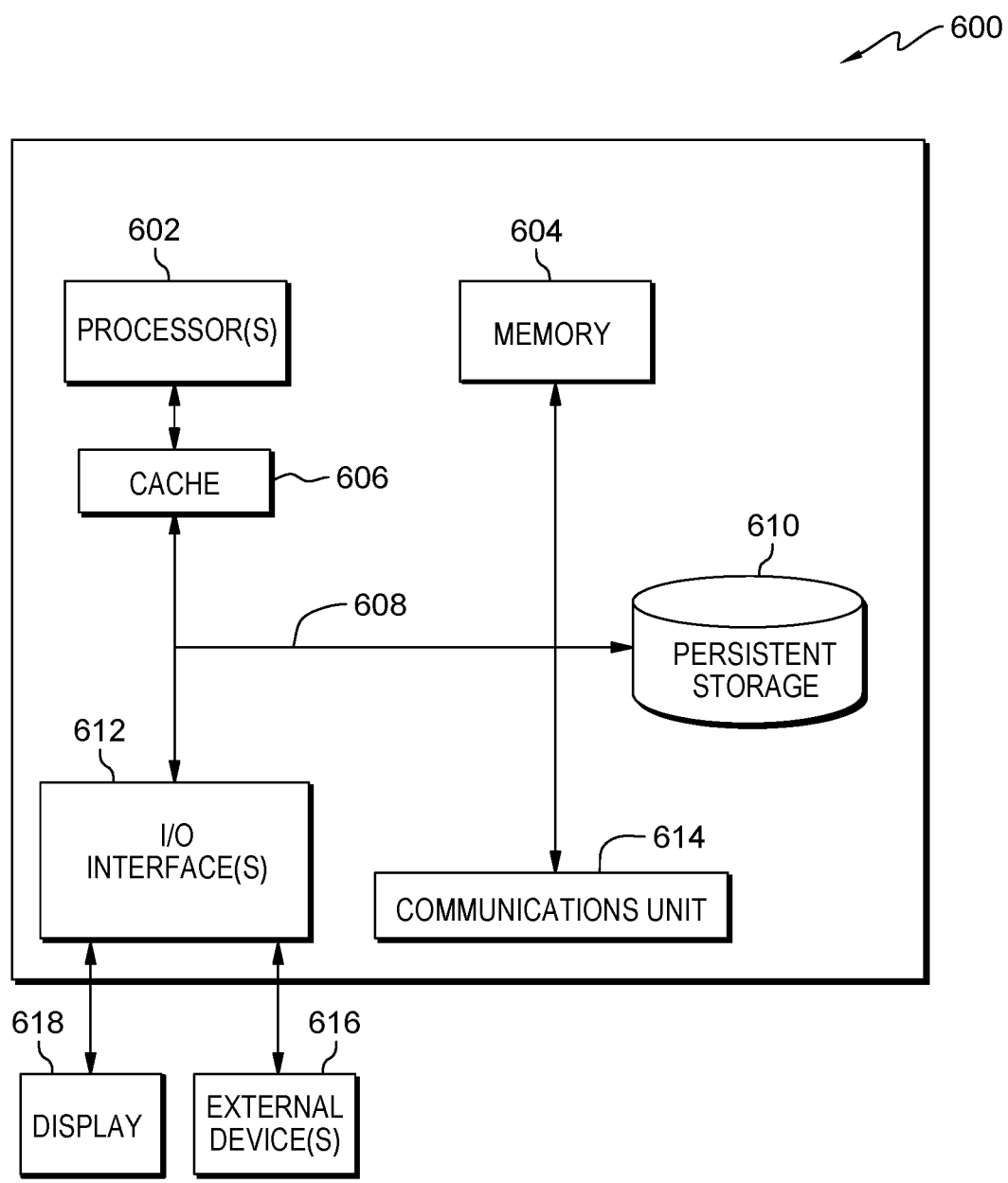
FIG. 6 is a block diagram of components of a computing device executing operations according to embodiments of the present invention.

FIG. 6 is a block diagram of components of a computing device, generally designated 600, in accordance with an embodiment of the present invention. In one embodiment, computing system 600 is representative of activity recommendation server 110 within computing environment 100, in which case activity recommendation server 110 includes activity recommendation program 300.

It should be appreciated that FIG. 6 provides only an illustration of one implementation and does not imply any limitations with regard to the environments in which different embodiments may be implemented. Many modifications to the depicted environment may be made.

Computing system 600 includes processor(s) 602, cache 606, memory 604, persistent storage 610, input/output (I/O) interface(s) 612, communications unit 614, and communications fabric 608. Communications fabric 608 provides communications between cache 606, memory 604, persistent storage 610, communications unit 614, and input/output (I/O) interface(s) 612. Communications fabric 608 can be implemented with any architecture designed for passing data and/or control information between processors (such as microprocessors, communications, and network processors, etc.), system memory, peripheral devices, and any other hardware components within a system. For example, communications fabric 608 can be implemented with one or more buses or a crossbar switch.

Memory 604 and persistent storage 610 are computer readable storage media. In this embodiment, memory 604 includes random access memory (RAM). In general, memory 604 can include any suitable volatile or non-volatile computer readable storage media. Cache 606 is a fast memory that enhances the performance of processor(s) 602 by holding recently accessed data, and data near recently accessed data, from memory 604.

Program instructions and data used to practice embodiments of the present invention may be stored in persistent storage 610 and in memory 604 for execution by one or more of the respective processor(s) 602 via cache 606. In an embodiment, persistent storage 610 includes a magnetic hard disk drive. Alternatively, or in addition to a magnetic hard disk drive, persistent storage 610 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 610 may also be removable. For example, a removable hard drive may be used for persistent storage 610. Other examples include optical and magnetic disks, thumb drives, and smart cards that are inserted into a drive for transfer onto another computer readable storage medium that is also part of persistent storage 610.

Communications unit 614, in these examples, provides for communications with other data processing systems or devices. In these examples, communications unit 614 includes one or more network interface cards. Communications unit 614 may provide communications through the use of either or both physical and wireless communications links. Program instructions and data used to practice embodiments of the present invention may be downloaded to persistent storage 610 through communications unit 614.

I/O interface(s) 612 allows for input and output of data with other devices that may be connected to computer system 600. For example, I/O interface(s) 612 may provide a connection to external device(s) 616 such as a keyboard, keypad, a touch screen, and/or some other suitable input device. External device(s) 616 can also include portable computer readable storage media such as, for example, thumb drives, portable optical or magnetic disks, and memory cards. Software and data used to practice embodiments of the present invention can be stored on such portable computer readable storage media and can be loaded onto persistent storage 610 via I/O interface(s) 612. I/O interface(s) 612 also connect to display 618.

Display 618 provides a mechanism to display or present data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Some helpful definitions follow:

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

User/subscriber: includes, but is not necessarily limited to, the following: (i) a single individual human; (ii) an artificial intelligence entity with sufficient intelligence to act as a user or subscriber; and/or (iii) a group of related users or subscribers.

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine-readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer-implemented method comprising:
   monitoring a physical activity performed by a user wearing an activity tracker during a period of time;
   receiving activity data from the activity tracker, the activity tracker tracking physical movement of the user during the period of time;
   determining environmental data in which the physical activity occurs for the period of time;
   receiving physical data describing physical conditions of the user while performing the physical activity;
   generating a physical activity model that correlates the activity data, the environmental data, and the physical data chronologically over the period of time;
   identifying a weather forecast for a geographic region in which the user will be located at a specified time of day;
   determining, for the specified time of day, a set of physical activities for the user to perform including the physical activity based on the weather forecast, the set of physical activities being selected according to the environmental data and corresponding physical data indicating a positive outcome historically with similar weather as in the weather forecast; and
   generating a schedule for user to perform the physical activity during the specified time of day, the schedule being determined by the physical activity model according to the weather forecast, the schedule including an activity period for performing the physical activity within the specified time of day for which the weather forecast was identified.

2. The method of claim 1, further comprising:
   identifying the physical activity from a table of potential activities and corresponding physical movement associated with the physical activity.

3. The method of claim 1, further comprising:
   determining a performance level during the period of time, the performance level indicating a degree of efficiency in performing the physical activity according to the activity data and the physical data; and
   associating the performance level with the physical activity in the physical activity model.

4. The method of claim 3, further comprising:
   determining a desired performance level for the physical activity;
   wherein the physical activity model requires a predicted performance level during the schedule to be at least as high as the desired performance level.

5. The method of claim 1, further comprising:
  determining the physical activity is being performed during a second period of time;
  receiving additional activity data from the activity tracker during the second period of time;
  determining additional environmental data during the second period of time;
  receiving additional physical data during the second period of time; and
  responsive to the end of the second period of time, revising the physical activity model correlate the additional activity data, the additional environmental data, and the additional physical data.

6. A computer program product comprising a computer-readable storage medium having a set of instructions stored therein which, when executed by a processor, causes the processor to generate a schedule for performing a physical activity by:
  monitoring a physical activity performed by a user wearing an activity tracker during a period of time;
  receiving activity data from the activity tracker, the activity tracker tracking physical movement of the user during the period of time;
  determining environmental data in which the physical activity occurs for the period of time,
  receiving physical data describing physical conditions of the user while performing the physical activity;
  generating a physical activity model that correlates the activity data, the environmental data, and the physical data chronologically over the period of time;
  identifying a weather forecast for a geographic region in which the user will be located at a specified time of day;
  determining, for the specified time of day, a set of physical activities for the user to perform including the physical activity based on the weather forecast, the set of physical activities being selected according to the environmental data and corresponding physical data indicating a positive outcome historically with similar weather as in the weather forecast; and
  generating a schedule for user to perform the physical activity during the specified time of day, the schedule being determined by the physical activity model according to the weather forecast, the schedule including an activity period for performing the physical activity within the specified time of day for which the weather forecast was identified.

7. The computer program product of claim 6, further causing the processor to generate a schedule for performing a physical activity by:
  identifying the physical activity from a table of potential activities and corresponding physical movement associated with the physical activity.

8. The computer program product of claim 6, further causing the processor to generate a schedule for performing a physical activity by:
  determining a performance level during the period of time, the performance level indicating a degree of efficiency in performing the physical activity according to the activity data and the physical data; and
  associating the performance level with the physical activity in the physical activity model.

9. The computer program product of claim 8, further causing the processor to generate a schedule for performing a physical activity by:
  determining a desired performance level for the physical activity;
  wherein the physical activity model requires a predicted performance level during the schedule to be at least as high as the desired performance level.

10. The computer program product of claim 6, further causing the processor to generate a schedule for performing a physical activity by:
  determining the physical activity is being performed during a second period of time;
  receiving additional activity data from the activity tracker during the second period of time;
  determining additional environmental data during the second period of time;
  receiving additional physical data during the second period of time; and
  responsive to the end of the second period of time, revising the physical activity model correlate the additional activity data, the additional environmental data, and the additional physical data.

11. A computer system for generating a schedule for performing a physical activity, the computer system comprising:
  a processor set; and
  a computer readable storage medium;
  wherein:
  the processor set is structured, located, connected, and/or programmed to run program instructions stored on the computer readable storage medium; and
  the program instructions which, when executed by the processor set, cause the processor set to generate a schedule for performing a physical activity by:
    monitoring a physical activity performed by a user wearing an activity tracker during a period of time;
    receiving activity data from the activity tracker, the activity tracker tracking physical movement of the user during the period of time;
    determining environmental data in which the physical activity occurs for the period of time,
    receiving physical data describing physical conditions of the user while performing the physical activity;
    generating a physical activity model that correlates the activity data, the environmental data, and the physical data chronologically over the period of time;
    identifying a weather forecast for a geographic region in which the user will be located at a specified time of day;
    determining, for the specified time of day, a set of physical activities for the user to perform including the physical activity based on the weather forecast, the set of physical activities being selected according to the environmental data and corresponding physical data indicating a positive outcome historically with similar weather as in the weather forecast; and
    generating a schedule for user to perform the physical activity during the specified time of day, the schedule being determined by the physical activity model according to the weather forecast, the schedule including an activity period for performing the physical activity within the specified time of day for which the weather forecast was identified.

12. The computer system of claim 11, further causing the processor set to generate a schedule for performing a physical activity by:
  identifying the physical activity from a table of potential activities and corresponding physical movement associated with the physical activity.

13. The computer system of claim 11, further causing the processor set to generate a schedule for performing a physical activity by:
- determining a performance level during the period of time, the performance level indicating a degree of efficiency in performing the physical activity according to the activity data and the physical data; and
- associating the performance level with the physical activity in the physical activity model.

14. The computer system of claim 13, further causing the processor set to generate a schedule for performing a physical activity by:
- determining a desired performance level for the physical activity;
- wherein the physical activity model requires a predicted performance level during the schedule to be at least as high as the desired performance level.

15. The computer system of claim 11, further causing the processor set to generate a schedule for performing a physical activity by:
- determining the physical activity is being performed during a second period of time;
- receiving additional activity data from the activity tracker during the second period of time;
- determining additional environmental data during the second period of time;
- receiving additional physical data during the second period of time; and
- responsive to the end of the second period of time, revising the physical activity model correlate the additional activity data, the additional environmental data, and the additional physical data.

* * * * *